United States Patent
Selai et al.

(10) Patent No.: US 6,866,772 B2
(45) Date of Patent: Mar. 15, 2005

(54) EXTRACTION OF AROMATICS FROM HYDROCARBON OIL USING FURFURAL-CO-SOLVENT EXTRACTION PROCESS

(75) Inventors: Raman Naduhatty Selai, Haryana (IN); Devotta Irudayaraj, Haryana (IN); Bhaskar Mani, Haryana (IN); Venketesan Phoobalan, Haryana (IN); Rewat Bijendra Singh, Haryana (IN); Rawat Bachan Singh, Haryana (IN); Bhatnagar Akhilesh Kumar, Haryana (IN)

(73) Assignee: Indian Oil Corporation Limited, Mumbai (IN)

( * ) Notice: Subject to any disclaimer, the term of this patent is extended or adjusted under 35 U.S.C. 154(b) by 0 days.

(21) Appl. No.: 09/871,077

(22) Filed: May 31, 2001

(65) Prior Publication Data

US 2003/0100813 A1 May 29, 2003

(30) Foreign Application Priority Data

Jan. 9, 2001 (IN) ..................................... 25/MUM/2001

(51) Int. Cl.$^7$ ......................... C10G 21/02; C10G 21/12; C10G 21/20; C07C 7/08
(52) U.S. Cl. ........................ 208/327; 208/311; 208/322; 208/323; 208/326; 585/860; 585/864
(58) Field of Search ................................ 208/311, 313, 208/322, 323, 327, 326; 585/860, 864

(56) References Cited

U.S. PATENT DOCUMENTS 3,929,617 A * 12/1975 Henry et al. ................... 208/96

* cited by examiner

Primary Examiner—Walter D. Griffin
Assistant Examiner—Tam M. Nguyen
(74) Attorney, Agent, or Firm—RatnerPrestia

(57) ABSTRACT

An improved furfural extraction process for lube oil basestock production from hydrocarbon oils containing aromatic type material by the addition of a solvent comprising of furfural and a co-solvent, said process being conducted in a continuous countercurrent extraction column that facilitates phase separation and increases the raffinate yield while maintaining the same raffinate quality measured by raffinate refractive index.

18 Claims, No Drawings

EXTRACTION OF AROMATICS FROM HYDROCARBON OIL USING FURFURAL-CO-SOLVENT EXTRACTION PROCESS

FIELD OF THE INVENTION

The invention relates to extraction of aromatics from hydrocarbon oils using furfural-co-solvent mixture to improve the selectivity. Use of this furfural-co-solvent mixture as solvent produces same quality raffinate as those of neat furfural measured by the refractive index, but produces higher yield of raffinate at same solvent to feed treat ratio.

BACKGROUND AND PRIOR ART REFERENCES TO THE INVENTION

Solvent extraction is a process that separates hydrocarbon mixtures into two phases, a raffinate phase which contains substances of relatively high hydrogen to carbon ratio often called paraffinic type materials and an extract phase which contains substances of relatively low hydrogen to carbon ratio often called aromatic type materials. Therefore, it may be said that solvent extraction is possible because different liquid compounds have different solution affinities for each other and some combinations are completely miscible while other combinations are almost immiscible. The ability to distinguish between high carbon to hydrogen aromatic type and low carbon to hydrogen paraffinic type materials is termed selectivity. The more fine the distinguishment is done, the higher is the selectivity of the solvent.

Solvent extraction of hydrocarbon oils using polar solvents to remove aromatic constituents has long been a standard processing procedure in the Oil Industry. The use of furfural to selectively extract aromatic components from hydrocarbon oils is the subject of many patent, for instance, U.S. Pat. No. 2,079,885, U.S. Pat. No. 2,698,276, U.S. Pat. No. 3,567,627 and U.S. Pat. No. 4,571,295, which are incorporated by reference. In U.S. Pat. No. 5,922,193, ethers or aldehydes is added to furfural to improve the solvent capacity for debottlenecking the extraction unit and claimed 2–3 vol % increase in the raffinate yield during the process. In the prior art, U.S. Pat. No. 4,273,645 additives such as, sodium dodecylbenzene sulfonate or high molecular weight polyethylene oxide resin is added to improve the selectivity of furfural and claimed less than 3 vol % increase in the raffinate yield at solvent dosage of 250 vol %. Further, in the said prior art, the recovery and material balance of the additive employed is not disclosed.

OBJECTS OF THE INVENTION

The main object of the invention is to provide an improved process for the extraction of aromatic type material from hydrocarbon oil containing aromatic material by contacting the hydrocarbon oil with a solvent comprising furfural and a co-solvent.

Another object of the present invention is to provide an improved process for the extraction of aromatic type material from lube distillate containing aromatic material.

Yet another object of the invention is to provide a method employing a co-solvent comprising one or more aliphatic amides having carbon chain of less than 5 carbon atoms.

Still another object of the invention is to provide a method employing a co-solvent comprising one or more aliphatic amides having carbon chain of less than 3 carbon atoms.

One more object of the invention is to provide a furfural extraction process for lube oil based stock production from hydrocarbon oils employing furfural and a co-solvent in a continuous countercurrent extraction column.

One another object of the invention is to provide a furfural extraction process with a co-solvent to facilitate phase separation and to increase raffinate yield, while maintaining the product quality as measured by raffinate refractive index.

DETAILED DESCRIPTION OF THE INVENTION

The present invention relates to an improved furfural extraction process for the removal of aromatics from a hydrocarbon oil containing aromatic material and more particularly from a lube distillate containing aromatic material by the addition, in a unit, of a solvent comprising furfural and a co-solvent. Addition of the co-solvent to furfural, conducted in a continuous countercurrent extraction column facilitates phase separation and increases raffinate yield while maintaining the same raffinate quality measured by raffinate refractive index. In this process, addition of a co-solvent, preferably comprising one or more aliphatic amides to furfural is done to facilitate phase separation and selectivity, wherein the raffinate yield increases by more than 3 vol % and preferably, more than 5 vol % at solvent dosage of less than 250 vol %, preferably less than 180 vol % and more preferably less than 150% vol.

The invention therefore, includes an improved method for the production of lubricant base oil from hydrocarbon oil containing aromatic compounds, said process comprising contacting the hydrocarbon oil with a solvent comprising furfural and a co-solvent, preferably comprising of one or more aliphatic amides having carbon chain of less than five, and more preferably less than three carbon atoms under extraction conditions, producing a raffinate product with increased yield of more than 3 vol % and preferably more than 5 vol %. The invention further includes the co-solvent employed is recovered along with furfural and reused in the process.

In an embodiment, the present invention provides an improved furfural extraction process for the extraction of aromatic type material from a hydrocarbon oil and more particularly from a lube distillate containing aromatic material, said process comprising contacting, in a unit, the hydrocarbon oil with a solvent comprising of furfural and a co-solvent selected from one or more aliphatic amides having less than 5 carbon atoms, to obtain increased raffinate yield by facilitating phase separation, while maintaining the same product quality as measured by raffinate refractive index.

In a preferred embodiment of the present invention, the hydrocarbon oil is a lube distillate containing aromatic type material.

In another embodiment of the present invention, the aliphatic amide comprises of carbon chain having less than 3 carbon atoms.

In still another embodiment of the present invention, the hydrocarbon oil is selected from hydrocarbons having boiling point in the range of 300° C. to 600° C.

In yet another embodiment of the present invention, the hydrocarbon oil is selected from hydrocarbons having boiling point in the range of 370° C. to 565° C.

In still yet another embodiment of the present invention, the co-solvent is selected from the group comprising of formamide, N-methyl formamide, N,N Dimethyl formamide, acetamide, N-methyl acetamide, N,N Dimethyl acetamide, propionamide, N-methyl propionamide, and N,N Dimethyl propionamide.

In one more embodiment of the present invention, the ratio of furfural to the co-solvent is in the range of 70:30 to 95:5.

In one another embodiment of the present invention, the yield of raffinate increases by more than 3 vol %.

In one another preferred embodiment of the present invention, the yield of raffinate increases by more than 5 vol %.

In an embodiment of the present invention, the solvent dosage is less than 250 vol %.

In another embodiment of the present invention, the solvent dosage is less than 180 vol %.

In still another embodiment of the present invention, the solvent dosage is less than 150 vol %.

In yet another embodiment of the present invention, the furfural-co-solvent mixture shows improved stability.

The following description is given by way of illustration and should not be construed to limit the scope of the invention in any manner.

BRIEF DESCRIPTION OF THE ACCOMPANYING TABLES

Table 1 represents the properties of the co-solvent employed in the present invention.

Table 2 represents the properties of Inter-Neutral Distillate.

Table 3 represents the results from the continuous countercurrent extraction corresponding to Solvent to Feed ration of 1.5.

Table 4 represents the results from the continuous countercurrent extraction corresponding to Solvent to Feed ration of 1.8.

Feedstock

The process is applicable to hydrocarbon oils namely, vacuum gas oil, hydrotreated/hydrocracked oil and catalytic cracker bottom in the lubricant boiling range. The feedstocks invention. Since a feedstock contains aromatics usually ranging from at least about 25 vol %, specifically from 25 to 80 vol % and more specifically from 30 vol % to 60 vol %, the feedstock is initially subjected to an extraction step. Extraction utilizes a solvent, which is selective for aromatics, such as furfural in the present invention, and removes the aromatics, which contribute to poor stability and viscosity index. The solvent extraction is conducted with a solvent to oil ratio in the range of from about 0.5:1 to 10:1, such as in the range from about 0.75:1 to 5:1, depending on the feedstock. The operating conditions for furfural extraction cover a temperature range of about 25° C. to about 175° C., preferably from about 50° C. to 150° C. The yield in terms of volume percent typically ranges from 30 to 80. The characteristics of the product of solvent extraction are very important, and consideration of the solvent extraction conditions coupled with the choice of feed is necessary to achieve a product with the desired viscosity and VI, maximum yield of high VI product is achieved by adjusting the extraction severity. The resulting raffinate should have a VI of at least about 85, preferably 90. The aromatic-reduced raffinate should contain at most about 40 vol % aromatics, preferably ranging from about 10 to 30 vol %, even more preferably from 10 to 20 vol %. The extractions may be preformed by conventional means, such as in a multistage countercurrent system, in a column with packing material or provided with perforated plates or in a column with a rotating shaft provided with discs.

Solvent

The process of the present invention involves the addition of a co-solvent preferably an aliphatic amide or mixture of amides to furfural to facilitate phase separation and selectivity. The process of the present invention involves the addition of small volumes of one or more co-solvents to furfural to increase raffinate yield. The properties of the co-solvent employed for the present invention are listed in Table 1.

TABLE 1

| S. No. | Name of the solvent | Melting point in ° C. | Boiling point in ° C. | RI @ 20° C. | Density @ 20° C. gm/ml |
|---|---|---|---|---|---|
| 1. | Formamide | 2–3 | 210 | 1.447 | 1.134 |
| 2. | N-Methyl Formamide | −4 | 198–199 | 1.432 | 1.001 |
| 3. | N,N Di Methyl Formamide | −61 | 153 | 1.431 | 0.945 |
| 4. | Acetamide | 79–91 | 221 | — | — |
| 5. | N-Methyl Acetamide | 26–28 | 204–206 | 1.433 | 0.957 |
| 6. | N,N-Di Methyl Formamide | −20 | 164.5–166 | 1.438 | 0.937 |
| 7. | Propionamide | 80–83 | 213 | — | 1.042 |
| 8. | N-Methyl Propionamide | −43 | 79 | 1.377 | 0.915 |
| 9. | N, N Di Methyl Propionamide | −45 | 174–175 | 1.440 | 0.920 | may typically comprise hydrocarbons having initial boiling point of greater than 300° C. and a final boiling point of about 600° C., preferably those fractions having a boiling range of about 370° C. to 565° C. These lube distillate stocks namely, light neutral, interneutral and heavy neutral and are usually referred as solvent neutrals and are the distillate fractions of the vacuum tower.

Solvent Extraction

Solvent extraction is conducted by contacting the lube distillate with a selective solvent, furfural in the present Generally, the co-solvent is added in an amount less than about 30 vol % based on total solvent such as less than about 20 vol % based on total solvent, less than about 10 vol % based on total solvent and less than about 5 vol % based on total solvent, depending on the feedstock. For example, a 10 vol % co-solvent 90 vol % furfural blend may be used in the extraction process of the present invention when the feedstock is Arab mix Interneutral distillate. Co-solvents used in the process of the present invention also have a boiling point in the range of from about 50° C. to 225° C., preferably in the range of from about 75° C. to 200° C. The addition of co-solvents, such as N-Methyl Acetamide to furfural improves its selectivity for extraction of aromatics from lube distillates. Use of co-solvents in furfural extraction increases the raffinate yield at the same raffinate refractive index (RI).

In essence, the invention includes an improved method for the production of lubricant base oil from an aromatic containing hydrocarbon oil comprising contacting the hydrocarbon oil, with a solvent comprising furfural and a co-solvent, preferably an aliphatic amide or mixture of amides having a aliphatic carbon chain less than five and more preferably less than three under extraction conditions, producing a raffinate product with increased yield of more than 3 vol % and preferably more than 5 vol %. The invention further includes the co-solvent employed is recovered along with furfural and reused in the process.

The advantage of the present invention allows for retrofitting existing equipment. An additional advantage of the furfural/co-solvent mixture of the present invention is the lower operating cost as the cost of the co-solvent employed is lower than that of neat furfural. The addition of the co-solvent of the present invention also improves the stability of the resultant co-solvent-furfural blend compared to furfural alone preventing degradation of furfural, which results in lower furfural loss.

DESCRIPTION OF THE PREFERRED EMBODIMENT

The following example illustrates preferred embodiment of the process of the present invention. Arab mix Interneutral distillate having the properties as set forth below in Table 2, was used for each extraction example.

EXAMPLE 1

For each furfural, with or without co-solvent, continuous countercurrent extraction was performed in a 3-meter height bench scale jacketed glass column extraction apparatus. The feed, Arab mix distillate was heated and pumped for example. 1.0 kg hr from bottom of the extractor (feed inlet) and the solvent, furfural with or without co-solvent were heated and pumped for example, 1.5 kg/hr at the top of the extractor (solvent inlet). The solvent rate was varied accordingly to the desired solvent to freed weight ratios of 1:1.5 and 1:1.8. (These ratios are typically referred to as 150% and 180% solvent dosage). The extractions were performed at column top temperature for example, 110° C. and column bottom temperature for example 70° C. After the mixture of solvent and oil pumping started from their respective inlets, the raffinate phase from the top of the column (raffinate product phase outlet) and extract phase from the bottom of the column (extract product phase outlet) were drawn continuously. The interface between the lighter raffinate phase and heavier extract phase flow. After steady state, say, after 1 to 2 hrs, indicated by constant interface level and constant raffinate and extract phases flow, the raffinate phase and the extract phase were collected simultaneously for a given period of time say, 30 to 40 minutes, in all three to four batches. The two phases collected were weighed to ensure material balance closure. The solvent was stripped from the extract and raffinate with nitrogen under vacuum. The stripped raffinate and extract phases were weighed and the raffinate yield was obtained. Final raffinate samples were analyzed for, Density, API gravity, and Refractive Index (RI).

TABLE 2

Properties of Inter-Neutral Distillate

| S. No. | Properties | Result |
|---|---|---|
| 1. | Density @ 15° C., gm/ml | 0.9385 |
| 2. | API Gravity | 19.3 |
| 3. | Refractive Index at 60° C. | 1.50197 |
| 4. | Kinematic Viscosity, cSt at | |
| | 60° C. | 50.07 |
| | 100° C. | 9.25 |
| 5. | Distillation (ASTM D 1160), ° C. | |
| | IBP/5% vol rec., | 364/405 |
| | 50/90 | 471/519 |
| | 95 | 537 |

The results from the continuous countercurrent extraction are shown below in Table 3 and Table 4 corresponding to two Solvent to Feed ratio's (S/F ratio) 1.5 and 1.8, respectively while the rest of the operating parameters are kept constant.

Commercially, lube extraction units are operated to a RI specification since for a particular lube crude and type of refining process, raffinate R1 correlates with the viscosity index (VI) of the de-waxed oil (DWO), with lower R1 corresponding to higher VI. Analysis of the data in Table 3 shows that for extraction conducted at solvent to feed treat ratio of 1.5 or solvent dosage of 150 vol %, the co-solvent-furfural blends are more effective than furfural alone, resulting in more than 3 vol % improvement in raffinate yield at same raffinate RI. Similarly, the Table 4 shows an increase of more than 5 vol % of raffinate yield at same R1 at solvent to feed treat ratio of 1.8 or solvent dosage of 180 vol %.

TABLE 3

Countercurrent extraction experimental conditions and Products Properties

| Properties | Furfural | Furfural with Co-solvent |
|---|---|---|
| Experimental conditions | | |
| Column Top temperature, ° C. | 110 | 110 |
| Column Bottom temperature, ° C. | 70 | 70 |
| S/F ratio (wt/wt) | 1.5 | 1.5 |
| Raffinate Properties | | |
| Raffinate Yield, vol % | 67.8 | 71.2 |
| RI at 60° C. | 1.4729 | 1.4727 |
| Density @ 15° C., gm/ml | 0.8874 | 0.8871 |
| API Gravity | 28.0 | 28.0 |
| Extract Properties | | |
| Density @ 15° C., gm/ml | 1.0300 | 1.0305 |
| API Gravity | 5.9 | 5.8 |

TABLE 4

Countercurrent extraction experimental conditions and Products Properties

| Properties | Furfural | Furfural with Co-solvent |
|---|---|---|
| Experimental conditions | | |
| Column Top temperature, ° C. | 110 | 110 |
| Column Bottom temperature, ° C. | 70 | 70 |
| S/F ratio (wt/wt) | 1.8 | 1.8 |

TABLE 4-continued

Countercurrent extraction experimental conditions and Products Properties

| Properties | Furfural | Furfural with Co-solvent |
|---|---|---|
| Raffinate Properties | | |
| Raffinate Yield, vol % | 63.8 | 69.7 |
| RI at 60° C. | 1.4701 | 1.4697 |
| Density (fl), 15° C., gm/ml | 0.8835 | 0.8827 |
| API Gravity | 28.7 | 2S.8 |
| Extract properties | | |
| Density @ 15° C., gm/ml | 1.0243 | 1.0248 |
| API Gravity | 6.6 | 6.6 |

What is claimed is:

1. A process for the extraction of aromatic material from lube oil distillate, the process comprising:

contacting the lube oil distillate with a solvent and producing an extract phase and a raffinate product phase; and separating the extract phase from the raffinate product phase;

in which:

the lube oil distillate comprises 25 to 80 vol % of the aromatic material;

the solvent comprises furfural and a co-solvent capable of facilitating phase separation;

the co-solvent is N,N-dimethyl formamide; and the ratio of furfural to the co-solvent is in the range of 70:30 to 95:5.

2. The process of claim 1 additionally comprising the step of removing solvent from the raffinate product phase and forming a raffinate, in which the yield of the raffinate increases more than 3 vol % with the addition of the co-solvent compared to a furfural extraction process without the addition of the co-solvent.

3. The process of claim 2 in which the yield of the raffinate increases more than 5 vol %.

4. The process of claim 2 in which the product quality of the raffinate is maintained, as measured by raffinate refractive index.

5. The process of claim 1 in which the lube oil distillate has a boiling point in the range of 300° C. to 600° C.

6. The process of claim 1 in which the lube oil distillate has a boiling point in the range of 370° C. to 565° C.

7. The process of claim 1 in which the solvent dosage is less than 250 vol %.

8. The process of claim 1 in which the solvent dosage is less than 180 vol %.

9. The process of claim 1 in which the solvent dosage is less than 150 vol %.

10. The process of claim 6 in which the process is a continuous countercurrent extraction process.

11. The process for the extraction of aromatic material from lube oil distillate, the process comprising:

contacting the lube oil distillate with a solvent and producing an extract phase and a raffinate product phase; and separating the extract phase from the raffinate product phase;

in which:

the lube oil distillate comprises 25 to 80% of the aromatic material;

the solvent comprises furfural and a co-solvent capable of facilitating phase separation;

the co-solvent is N,N-dimethyl formamide;

the ratio of furfural to the co-solvent is in the range of 70:30 to 95:5 and the process is a continuous countercurrent extraction process.

12. The process of claim 11 additionally comprising the step of removing solvent from the raffinate product phase and forming a raffinate, in which the yield of the raffinate increases more than 3 vol % with the addition of the co-solvent compared to a furfural extraction process without the addition of the co-solvent.

13. The process of claim 12 in which the yield of the raffinate increases more than 5 vol %.

14. The process of claim 12 in which the product quality of the raffinate is maintained, as measured by raffinate refractive index.

15. The process of claim 11 in which the lube oil distillate has a boiling point in the range of 300° C. to 600° C.

16. The process of claim 11 in which the solvent dosage is less than 250 vol %.

17. The process of claim 9 in which the process is a continuous countercurrent extraction process.

18. The process of claim 11 in which the co-solvent is the solvent dosage is less than 150 vol %; the lube oil distillate has a boiling point in the range of 370° C. to 565° C.; and the yield of the raffinate increases more than 5 vol %.

* * * * *